(12) United States Patent
Noda

(10) Patent No.: US 9,500,629 B2
(45) Date of Patent: Nov. 22, 2016

(54) CHROMATOGRAM DATA PROCESSING METHOD AND DEVICE

(71) Applicant: SHIMADZU CORPORATION, Kyoto-shi, Kyoto (JP)

(72) Inventor: Akira Noda, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 679 days.

(21) Appl. No.: 13/668,770

(22) Filed: Nov. 5, 2012

(65) Prior Publication Data

US 2014/0129169 A1    May 8, 2014

(51) Int. Cl.
G01N 30/86    (2006.01)

(52) U.S. Cl.
CPC ....... *G01N 30/8665* (2013.01); *G01N 30/8644* (2013.01)

(58) Field of Classification Search
USPC .......................................................... 702/89
See application file for complete search history.

(56) References Cited

U.S. PATENT DOCUMENTS

2008/0180447 A1*    7/2008    Bertoncini et al. ........ 345/440.1

FOREIGN PATENT DOCUMENTS

| JP | 05-181498 A | 7/1993 |
| WO | 2004/090526 A1 | 10/2004 |

OTHER PUBLICATIONS

Christin Christin, Optimized Time Alignment Algorithm for LC-MS Data: Correlation Optimized Warping Using Component Detection Algorithm-Selected Mass Chromatograms, Analytical Biochemistry, Department of Pharmacy, University of Groningen, A. Deusinglaan 1, 9713 AV Groningen, The Netherlands, Analytical Chemistry, vol. 80, No. 18, Sep. 15, 2008.*
Katharina Podwojski, Gene expression, Retention time alignment algorithms for LC/MS data must consider non-linear shifts, Advance Access publication Jan. 28, 2009, Published by Oxford University Press. All rights reserved, pp. 758-764.*

* cited by examiner

*Primary Examiner* — Tung Lau
(74) *Attorney, Agent, or Firm* — Sughrue Mion, PLLC

(57) ABSTRACT

Before executing a search for optimal correspondence relationship with a coarse-to-fine DP (dynamic programming) algorithm using time information of peaks appearing in a chromatogram as input data, a simplified linear correction is executed based on detection of start point and end point of the section in which the peaks are present. It is sufficient to correct only nonlinear time deviations in coarse-to-fine DP, and the space to be searched is thus narrowed down. In addition, in coarse stage DP, the number of pieces of data to be processed is reduced by selecting peaks based on peak intensity. Between coarse stage DP and fine stage DP, local inappropriate matching is eliminated by performing filtering processing in accordance with trend of time deviations over the entire chromatogram. The space to be searched in fine stage DP becomes narrow, which reduces the number of candidates to be searched and shortens the calculation time.

7 Claims, 5 Drawing Sheets

CHROMATOGRAM DATA PROCESSING METHOD AND DEVICE

TECHNICAL FIELD

The present invention relates to a chromatogram data processing method and device for processing chromatogram data obtained by chromatographic analysis of a gas chromatogram (GC), a liquid chromatograph (LC), or the like; more particularly, the present invention relates to a data processing method and device for correcting the retention times of peaks appearing in a chromatogram.

BACKGROUND ART

In GC analysis, even if analysis is performed with the same device and under the same conditions, there is sometimes deviation in the retention times of the same component due to various factors such as fluctuations in the carrier gas flow rate over time and column deterioration. Therefore, in order to compare a plurality of chromatograms, an operation is required to correct the time axis so that the retention times of the same component are aligned roughly uniformly prior to this comparison. Although the correction of the time axis is easy if the deviation in the retention times is completely linear, deviations in retention times more often than not have nonlinearity. As one means for correcting the time axis to accommodate such nonlinear deviations in retention times, algorithms based on dynamic programming (abbreviated below as "DP") have been proposed conventionally (see Non-Patent Document 1 and Patent Document 1).

A DP algorithm that is typically used conventionally is a technique for coordinating a reference signal (reference chromatogram signal) serving as a standard and a target signal (target chromatogram signal) for which the time axis has been distorted nonlinearly, using the degree of distortion in time and the degree of matching of the intensities at corresponding points as a cost function, and finding a correspondence relationship between the reference signal and the target signal in which the calculated cost is minimized. If such a correspondence relationship can be found, it is possible to correct deviations in retention times by nonlinearly expanding and contracting the time axis of the target signal using the correspondence relationship.

Here, for the purpose of the explanation, the reference signal will be defined as A, and a sample point at each time of the reference signal A will be expressed as $A(n)$ (where n is a positive integer). Similarly, the target signal will be defined as B, and a sample point at each time of the target signal B will be expressed as $B(n)$. A method for searching for the optimal (most favorably matching) correspondence relationship in typical DP is as follows (see FIG. 8).

[1] Taking into consideration the range of commonsense time fluctuations (taking into consideration the maximum values of various fluctuations), the sample point of the target signal B corresponding to the sample point $A(1)$ of the reference signal A may correspond to "no corresponding point" or to target signal $B(1)$ to $B(3)$, for example.

[2] Depending on where in the aforementioned range the sample point of the target signal B corresponding to the sample point $A(1)$ of the reference signal A lies, the group of sample points of the target signal B to which the next sample point $A(2)$ of the reference signal A may correspond will respectively differ. For example, if the sample point of the target signal B corresponding to the sample point $A(1)$ of the reference signal A is $B(1)$, the group of sample points of the target signal B to which the next sample point $A(2)$ may correspond becomes "no corresponding point" or target signal $B(2)$ to $B(4)$, and if the sample point of the target signal B corresponding to the sample point $A(1)$ of the reference signal A is $B(2)$, the group of sample points of the target signal B to which the next sample point $A(2)$ may correspond becomes "no corresponding point" or target signal $B(3)$ to $B(5)$.

Accordingly, as shown in FIG. 8, the potentially corresponding sample points increase like a tree diagram as n of the sample point $A(n)$ increases—that is, as time passes.

Assuming from a commonsense standpoint that there are m potentially corresponding candidates for each sample point when searching for an optimal correspondence relationship as described above (m=4 in the case of the example shown in FIG. 8), if the chromatogram consists of data for n sample points in total, the number of paths (that is, candidates for a correspondence relationship over the entire chromatogram) derived is approximately m to the $n^{th}$ power. Accordingly, the order of the number of candidates for a correspondence relationship between the reference signal A and the target signal B is $O(m^n)$, and it is necessary to calculate the cost of each candidate and select the candidate with the lowest cost.

However, there are limitations to the amount of calculations that can be processed due to limitations in the performance of the computer used for calculation or the calculation time, so it is not realistic to perform cost calculations by searching for all of an enormous number of candidates as described above. Therefore, a technique is ordinarily used in which the final number of candidates is limited to x candidates by leaving behind only the top x candidates at each stage of the search and deleting all other data. Such a technique is typically called beam limiting with a beam width x. Although the required processing time is shortened as the beam width x is narrowed, if the beam width x is made unnecessarily narrow, there is an increased probability of falling into a localized solution in which the matching in only the first half of the search is satisfactory and the matching in the second half is poor, and the method is typically weak with regard to noise and the like. Conversely, in order to provide resistance (robustness) against such noise, it is necessary to allow an enormous amount of time for calculation processing.

That is, when applying a typical DP algorithm such as that described in Non-Patent Document 1 or Patent Document 1 to the correction of the time axis of a chromatogram, it is not possible to appropriately match the target signal to the reference signal in a realistic amount of calculation processing time under unfavorable conditions such as a large number of peaks appearing in the chromatogram due to a large number of contained components, a large number of peaks due to poor S/N of the obtained signal, or extremely large fluctuations over time, which leads to the risk that the time axis may be corrected inaccurately. In particular, the probability that it will not be possible to accurately correct the time axis increases substantially in cases in which there are large fluctuations over time due to column replacement in GC analysis or cases in which a sample containing an enormous number of components such as gasoline or a perfume is analyzed.

PRIOR ART DOCUMENTS

PATENT DOCUMENT 1—International Publication WO 2004/090526 Pamphlet

PATENT DOCUMENT 2—Japanese Unexamined Patent Application Publication H5-181498

NON-PATENT DOCUMENT 1—Pravdova (V. Pravdova) and 2 others, "A comparison on two algorithms for warping of analytical signals," Analytical Chimica Acta, 456, 2002, p. 77-92

NON-PATENT DOCUMENT 2—Hiromitsu Miyazaki and 2 others, "Elastic matching algorithm for images based on coarse-to-fine DP," Proceedings of the Meeting on Image Recognition and Understanding (MIRU2004), July 2004

SUMMARY OF THE INVENTION

The present invention was conceived in order to solve the problems described above, and the main purpose of the present invention is to provide a chromatogram data processing method and device capable of correcting the time axis of a chromatogram within a reasonable processing time and with high precision even under unfavorable conditions such as a large number of contained components (number of peaks), large amounts of noise, and large fluctuations over time. The "chromatograms" described here include total ion current chromatograms and extracted ion chromatograms (mass chromatograms) obtained with a chromatograph mass spectrometer.

A representative technique known for increasing speed in DP is coarse-to-fine DP, which reduces both n and m in the number of candidates O (mn) by dividing the DP algorithm processing into two stages—a broad candidate search and a detailed candidate search. For example, in Patent Document 2, a technique which utilizes coarse-to-fine DP for voice recognition is disclosed. In Non-Patent Document 2, a method of utilizing coarse-to-fine DP for the recognition of image patterns with variations is proposed. In general, voice signals or image signals have the property that there is a high correlation between a signal value at a given position and a signal value at a position nearby temporally or spatially. Therefore, applying coarse-to-fine DP is comparatively easy. In contrast, in the case of chromatogram signals, there is virtually no correlation between a given peak and another peak nearby temporally, and it is not possible to directly use the coarse-to-fine DP for voice or images as described above. Accordingly, the inventor of this application conceived of the invention of this application as a result of introducing the coarse-to-fine DP technique to the correction of the time axis of a chromatogram while adding processing so as to minimize the amount of calculations of DP by utilizing the properties of chromatogram signals.

Specifically, the first invention, which was conceived in order to solve the problems described above, is a chromatogram data processing method which, for chromatogram data obtained by a chromatograph device comprising a separation part for separating various components contained in a sample in the time direction and a detector for detecting a sample with separated components, corrects the time axis of a reference chromatogram serving as a standard so as to align the time axis of a target chromatogram with the time axis of the reference chromatogram, the method comprising:

a) a linear correction step for eliminating linear time variation from the target chromatogram using peaks detected in the reference chromatogram and the target chromatogram;

b) a coarse searching step for searching for candidates for a correspondence relationship between the reference chromatogram and the target chromatogram in a coarse stage by selecting peaks for the respective reference chromatogram and target chromatogram based on the respectively detected peak intensities in the target chromatogram and the reference chromatogram after linear correction by the linear correction step and executing matching by a dynamic programming algorithm focusing on the retention times of the selected peaks;

c) a fine searching step for searching for a correspondence relationship between the reference chromatogram and the target chromatogram in a fine stage by adding the peaks eliminated in the coarse searching step and then executing matching by a dynamic programming algorithm focusing on the retention times of the peaks for the candidates for a correspondence relationship in the coarse stage extracted in the coarse searching step; and d) a correction processing step for correcting the time axis of the target chromatogram based on the correspondence relationship between the reference chromatogram and the target chromatogram extracted in the fine searching step.

In addition, the second invention is a device for implementing the chromatogram data processing method of the first invention which, for chromatogram data obtained by a chromatograph device comprising a separation part for separating various components contained in a sample in the time direction and a detector for detecting a sample with separated components, corrects the time axis of a reference chromatogram serving as a standard so as to align the time axis of a target chromatogram with the time axis of the reference chromatogram, the device comprising:

a) a linear correction means for eliminating linear time variation from the target chromatogram using peaks detected in the reference chromatogram and the target chromatogram;

b) a coarse searching means for searching for candidates for a correspondence relationship between the reference chromatogram and the target chromatogram in a coarse stage by selecting peaks for the respective reference chromatogram and target chromatogram based on the respectively detected peak intensities in the target chromatogram and the reference chromatogram after linear correction by the linear correction means and executing matching by a dynamic programming algorithm focusing on the retention times of the selected peaks;

c) a fine searching means for searching for a correspondence relationship between the reference chromatogram and the target chromatogram in a fine stage by adding peaks eliminated by the coarse searching means and then executing matching by a dynamic programming algorithm focusing on the retention times of the peaks for the candidates for a correspondence relationship in the coarse stage extracted by the coarse searching means; and d) a correction processing means for correcting the time axis of the target chromatogram based on the correspondence relationship between the reference chromatogram and the target chromatogram extracted by the fine searching means.

One of the most significant causes of deviations in retention time arising in a chromatogram is column degradation, but although there is some degree of fluctuation, deviations in retention time caused by this are primarily temporally linear deviations. That is, the deviations are such that the time axis of a target chromatogram is expanded by a factor of p (or reduced to 1/p) on the whole with respect to the time axis of a reference chromatogram and is further shifted on the whole by q. With the chromatogram data processing method and device of the present invention, the linear time deviations described above are reduced in advance by means of linear correction processing in the linear correction step before coarse-to-fine DP is executed. This makes it sufficient to correct only nonlinear retention time deviations in coarse-to-fine DP performed subsequently, which makes it possible to perform matching with sufficient robustness even with a limited beam width—that is, even if the searching space is narrowed.

In the typical coarse-to-fine DP described above, data of low time resolution is first generated by re-sampling calculation data, and coarse-to-fine DP is performed to reduce the number of data points (n) using this as input data. After m is then reduced by applying the restriction of not significantly going against the optimal correspondence relationship (matching) obtained at the low time resolution and then performing DP processing in the fine stage at the original (prior to re-sampling) time resolution. However, in the case of a chromatogram signal, the actual information held by the original signal is lost due to simple re-sampling. The important information in the case of a chromatogram signal is the positions (times) of the tops of peaks, so the positions (times) of detected peaks are used as input data for DP.

However, when there is a large number of contained components, the number of peaks also increases, and peaks caused by noise also appear in the chromatogram. Therefore, in the coarse searching step, the number of pieces of data to be processed is reduced and the effects of noise are simultaneously reduced by selecting only peaks with a particularly high probability of being useful for correction in order of intensity, for example, and using the peaks as input data for DP. The peak intensity used for this peak extraction may use the peak height and/or the peak area. As a result of the coarse searching step described above, candidates are found for a correspondence relationship between each peak extracted in the reference chromatogram and each peak extracted in the target chromatogram. That is, for each peak extracted in the reference chromatogram, one or a plurality of candidates of corresponding peaks in the target chromatogram are given.

Next, in the fine searching step, the candidates for a correspondence relationship are narrowed down by executing matching based on the candidates found in the coarse searching step, including the peaks excluded previously due to low intensity. For example, for the peaks in a reference chromatogram for which at least one corresponding peak candidate has been given in the coarse searching step, if one of the candidates is given as a candidate in the fine searching step, the candidate is considered to be the optimal solution and the other candidates are discarded. On the other hand, for peaks in a reference chromatogram with no corresponding peak candidates in the coarse searching step, a cost calculation for fine searching should be made using the provisional position (time) found by directly correcting the candidate at the closest position temporally.

With DP using two stages (coarse and fine), it is possible to find the most reliable correspondence relationship between each peak in the reference chromatogram and each peak in the target chromatogram. Next, in the correction processing step, the time axis of the target chromatogram is corrected based on the correspondence relationship described above. As a result, the entire signal waveform of the target chromatogram is corrected rather than only the positions of the tops of the peaks using the reference chromatogram as a standard.

The chromatogram data processing method of the first invention should also have a filtering step which, after the execution of the coarse searching step and before the execution of the fine searching step, uses the overall trend of matching as an evaluation criterion and removes matching results which do not conform to the evaluation criterion. As an overall matching trend, a statistical value of the overall amount of fluctuation should be used. For example, the standard deviation of the amount of fluctuation may be found, and this standard deviation can be used as an evaluation criterion.

As a result, candidates which are invalid as indicated by the overall trend can be removed in advance from the peak correspondence candidates given in the coarse searching step. Therefore, it is possible to effectively reduce the amount of calculation by cutting the number of candidates for a correspondence relationship, and it is also possible to increase the searching precision in the DP of the fine stage.

As one mode of the chromatogram data processing method of the first invention, the linear correction step may find a coefficient for linear correction by extracting a corresponding time range between the reference chromatogram and the target chromatogram using the intensity correlations and time relationships of a plurality of peaks close to one another in the time direction, investigating the degree of matching of peaks when performing linear correction while assuming combinations of the time ranges, and selecting the combination of time ranges which demonstrates the best match. Here, it is preferable to extract time ranges respectively corresponding to the head part and the tail end part of the reference chromatogram and the target chromatogram.

In addition, as a measure indicating the degree of matching of peaks in the linear correction step, for each peak in the reference chromatogram, the sum of the absolute values of time differences of a single peak in the reference chromatogram and a peak positioned closest to the aforementioned peak and falling within a certain intensity ratio range with respect to the intensity of the peak in the reference chromatogram in the target chromatogram after linear correction is performed under the assumptions described above may be used. As a result, it is possible to realize linear correction with high precision using comparatively simple operations.

With the chromatogram data processing method and device of the present invention, in order to correct the time axis of a chromatogram, coarse-to-fine DP which is improved so as to conform to the properties of chromatogram signals and situations in which time fluctuations arise is used, and correction is performed by removing linear time deviations prior to this coarse-to-fine DP, so it is possible to sufficiently match the target chromatogram to the reference chromatogram while efficiently reducing the number of candidates for a correspondence relationship. As a result, it is possible to correct the time axis in a sufficiently short period of time for practical applications and with high precision even under unfavorable conditions such as a large number of peaks due to a large number of components contained in a sample, poor signal S/N, and large fluctuations over time, for example. Accordingly, it becomes possible, for example, to compare multiple chromatograms with good precision.

In addition, since data processing has sufficient robustness, it is possible to process data obtained from various samples without changing the parameters required for data processing such as the weight of the cost function or the beam width at the time of coarse-to-fine DP in accordance with the types of samples or the analysis conditions. Therefore, the burden of the operator at the time of data processing is reduced, and the processing throughput is also improved.

DETAILED DESCRIPTION OF THE EXEMPLARY EMBODIMENTS

An embodiment of a gas chromatograph (GC) device using a chromatogram data processing device implementing the chromatogram data processing method of the present invention will be described with reference to the attached drawings.

Figure 1:
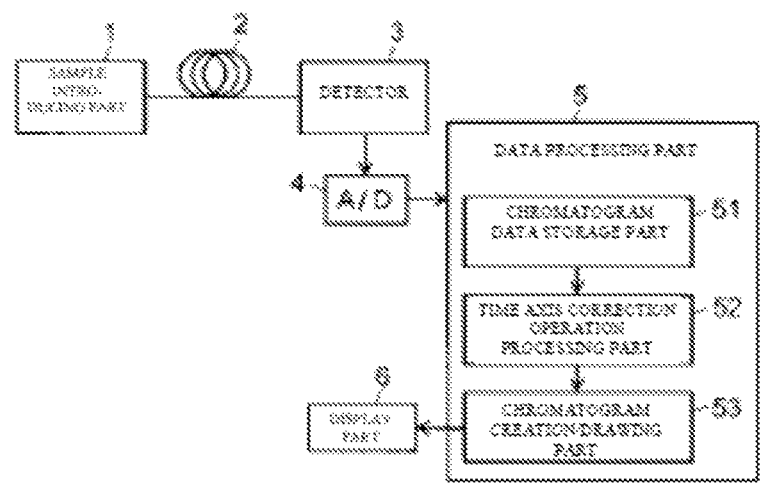
FIG. 1 is an overall schematic diagram of a GC device to which the chromatogram data processing device of the present invention is applied.

FIG. 1 is a schematic block diagram of the GC device of this embodiment. In FIG. 1, a carrier gas is supplied at a constant flow rate to a column 2 from a sample introducing part 1 including a sample vaporizing chamber or the like, and when a sample is infused into the sample introducing part 1, the sample is carried by the carrier gas flow and introduced into the column 2. Various components in the sample are separated in the time direction while the sample passes through the column 2 and are then sequentially eluted from the column 2 outlet and introduced into a detector 3. The detector 3 is a flame ionization detector (FID) or a mass spectrometer, for example, which constantly outputs a detection signal corresponding to the amount of the introduced sample components. This signal is converted to a digital value by an A/D converter 4 and inputted into a data processing part 5. The data processing part 5 comprises a chromatogram data storage part 51, a time axis correction operation processing part 52, a chromatogram creation/drawing part 53, and the like, and the created chromatogram is displayed on a display part 6.

The main part of the data processing part 5 is a personal computer, and the functions of each of the parts described above can be realized by operating dedicated data processing software installed in advance on the computer.

When chromatogram data is obtained by executing GC analysis of the same sample under the same analysis conditions using this GC device, the retention times of the same sample components will ideally always be the same. However, in actuality, fluctuations in the time axis arise due to various factors such as changes in the interactions between the sample components and the inside wall of the column 2 due to the degradation of the column 2 over time, temporal fluctuations in the flow rate of the carrier gas supplied to the column 2 from the sample introducing part 1, and temporal fluctuations in the heating rate of the column oven (not shown) in which the column 2 is housed, and it is often the case that the retention times for the same sample components are not constant. This becomes problematic when comparing a plurality of chromatograms, in particular. Therefore, the GC device of this embodiment is configured so as to correct the time axis of the chromatogram obtained by GC analysis by means of the following such time axis correction processing.

Figure 2:
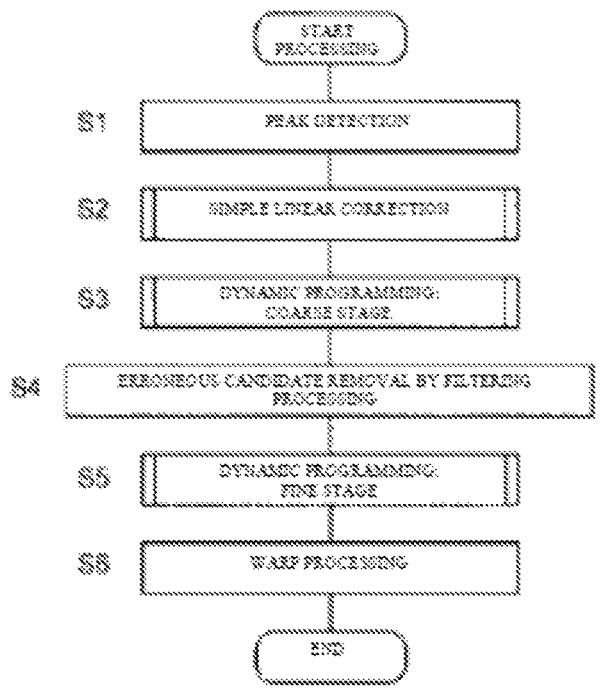
FIG. 2 is a flowchart showing the processing procedure of the time axis correction method characteristic to the present invention.

FIG. 2 is a flowchart showing the general procedure of the time axis correction processing executed by the time axis correction operation processing part 52. The time axis correction processing described here is processing for correcting the time axis of a target chromatogram obtained by GC analysis so as to match the time axis of a reference chromatogram stored in the chromatogram data storage part 51 using the reference chromatogram as a standard. The reference chromatogram and the target chromatogram are fundamentally obtained by analyzing the same type of sample.

As a procedure for correction processing, peak detection is first performed for the reference chromatogram and the target chromatogram, respectively, and the positions (times) and intensities (heights and/or areas) of the tops of peaks are obtained as peak information (step S1). The time information of the peaks detected here serve as input data for the coarse-to-fine DP described below.

Next, simple linear correction processing is executed in order to eliminate linear retention time deviations contained in the target chromatogram (step S2). As a result of this simple linear correction, the linear component including expansion/contraction by a factor of p in the time axis direction and a shift by time q is almost completely eliminated in the target chromatogram, and nonlinear retention time deviations are left behind. In actuality, linear correction should be performed for each peak in the target chromatogram so as to amend the time information of the peaks. Of course, it is also possible to correct linear time deviations in coarse-to-fine DP, but since linear time deviations are ordinarily substantially larger than nonlinear time deviations, the search space at the time of DP becomes quite large if linear and nonlinear deviations are mixed (overlapping). In contrast, the search space can be narrowed by eliminating linear time deviations in advance.

After simple linear correction, the number of peaks is reduced to a prescribed number by selecting peaks based on the intensity information of each peak in the reference chromatogram and the target chromatogram, respectively. The time information (time information after linear correction for the target chromatogram) of peaks after the number has been substantially reduced in comparison to the original number of peaks due to this selection is then used as input data, and a search is performed for candidates for a correspondence relationship between the reference chromatogram and the target chromatogram by performing matching based on a DP algorithm in the coarse stage (step S3).

After the candidate search by coarse stage DP is completed and before the next search by fine stage DP is performed, matching presumed to be obviously erroneous is eliminated from the candidates given in the search of the coarse stage by filtering processing using the validity of correction from the perspective of the overall trend as a criterion (step S4). As a criterion for assessing whether matching is erroneous, a statistical value of the overall amount of fluctuation in time deviations, for example, may be used. The number of candidates to be searched can be reduced by this filtering processing.

Next, using the matching results of coarse stage DP, peaks which were not selected in the peak selection described above—that is, peaks that were not considered in coarse stage DP—are added, and the candidates for a correspondence relationship given in coarse stage DP are ultimately narrowed down to one candidate by performing matching based on the DP algorithm of the fine stage (step S5). If an optimal correspondence relationship—that is, one involving the lowest cost—of the target chromatogram with respect to the reference chromatogram is found as a result of the search for candidates based on coarse-to-fine DP, a signal for which each sample point of the target chromatogram is moved—that is, a signal with a corrected time axis—is found by warp processing based on this result (step S6). As a result, chromatogram data in which the retention time deviations contained in the target chromatogram are corrected is obtained.

The series of processes described above will be described in detail with focus on the processing characteristic to the present invention.

Simple Linear Correction

Figure 3:
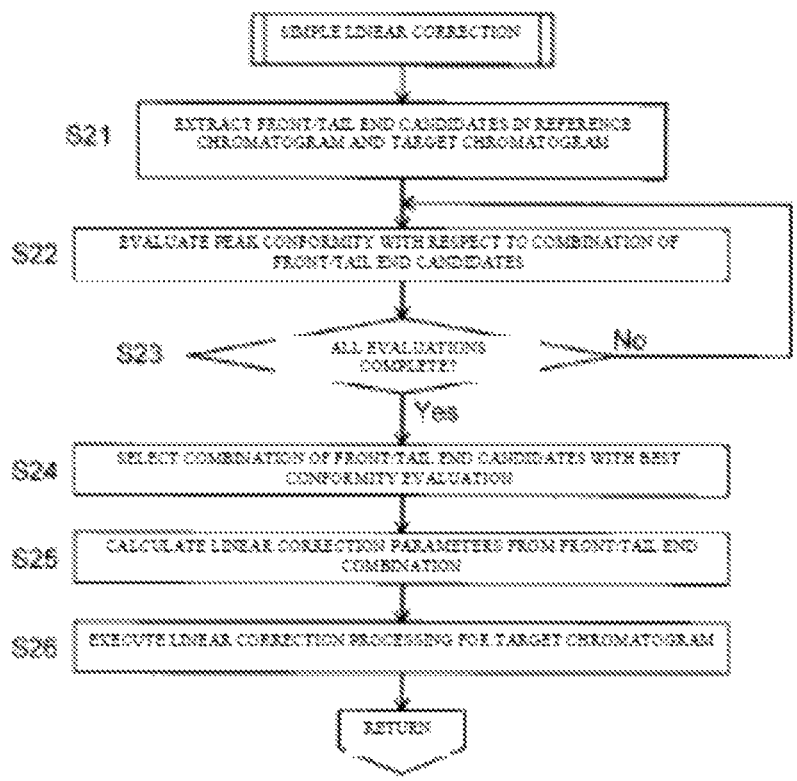
FIG. 3 is a flowchart of simple linear correction in FIG. 2.
Figure 4:
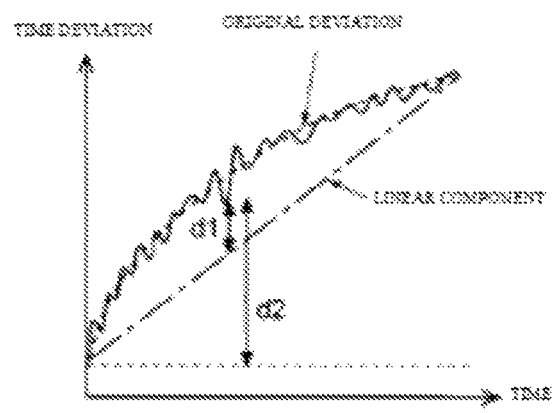
FIG. 4 is an explanatory diagram of the concept of simple linear correction.
Figure 5:
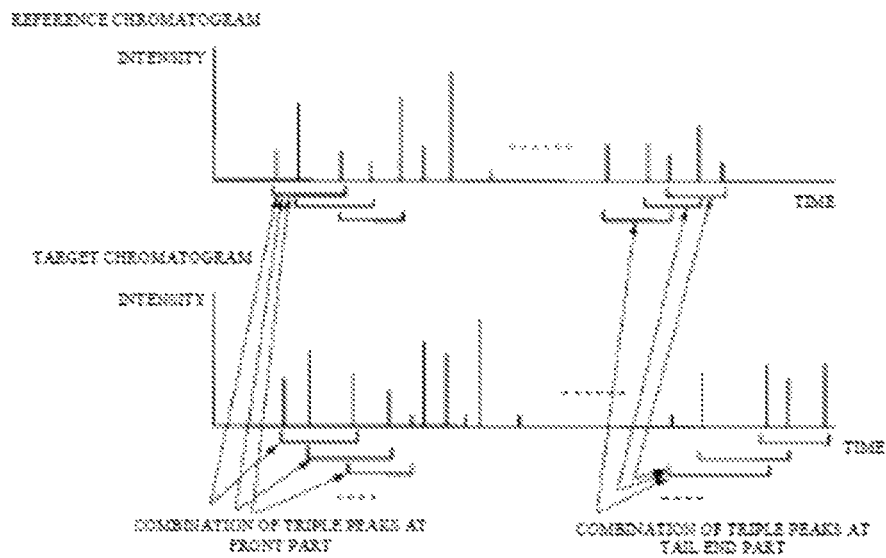
FIG. 5 is an explanatory diagram of the processing of simple linear correction.

The main cause of retention time deviations in a chromatogram is the degradation of the column 2, and although there is some degree of fluctuation, most retention time deviations caused by this are linear. That is, the general trend of the time deviations of the target chromatogram with respect to the reference chromatogram is rectilinear. Therefore, by eliminating linear retention time deviations before attempting to correct the time axis by DP, it is possible to reduce the burden of correction by DP and improve the correction precision. FIG. 3 is a flowchart showing the procedure for simple linear correction processing. FIG. 4 is an explanatory diagram of the concept of simple linear correction. FIG. 5 is an explanatory diagram of the processing of simple linear correction.

As shown in FIG. 4, the linear component and the nonlinear component ordinarily overlap in the time deviations of a chromatogram, but the linear components are often dominant. It can be seen that if the linear component is not eliminated, the amount of deviation that must be corrected by coarse-to-fine DP is d2, whereas if the linear component is eliminated, the amount of deviation that must be corrected by coarse-to-fine DP is only d1.

The linear component of time deviations can be calculated from the start point and end point of the section where peaks are present in the chromatogram, but start point/end point detection with high resistance to noise and the like is necessary for this purpose. Here, by using a plurality of peaks appearing in the vicinity of one another temporally as one group and evaluating the similarity between the reference chromatogram and the target chromatogram, the start point and the end point of the section where the peaks are present in the two chromatograms are detected. In addition, the section where the peaks are present in the target chromatogram is expanded/contracted and shifted in the time axis direction so that the start point and end point of the section where the peaks are present in the target chromatogram match the start point and end point of the section where the peaks are present in the reference chromatogram.

That is, candidates for the front and the tail end are first extracted for the reference chromatogram and the target chromatogram, respectively, using a prescribed range in the vicinity of the start point and a prescribed range in the vicinity of the end point of the section where the peaks are present (step S21). Specifically, as shown in FIG. 5, three temporally consecutive peaks (triple peaks) are extracted, and the correlation coefficient $\alpha$ of the intensities of the three peaks and the ratio $\beta=T1/T2$ of the time interval $T1$ between the first peak and the second peak and the time interval $T2$ between the second peak and the third peak are found. The correlation coefficient $\alpha$ and the time interval ratio $\beta$ are parameters for assessing the conformity (similarity) of the triple peaks in the reference chromatogram and the triple peaks in the target chromatogram. The conformity of the triple peaks on the start point side of the reference chromatogram and the triple peaks on the start point side of the target chromatogram is then evaluated using the correlation coefficient $\alpha$ and the time interval ratio $\beta$, and peaks with a high probability of matching are selected and designated as candidates for the front end. Similarly, peaks with a high probability of matching among the triple peaks on the end point side of the reference chromatogram and the triple peaks on the end point side of the target chromatogram are selected and designated as candidates for the tail end.

Next, one of each of the candidates (triple peaks) for the front end and the candidates (triple peaks) for the tail end extracted in step S21 described above is selected, and a trial run of linear correction is actually performed on the target chromatogram under those conditions to assess the degree of matching of the peaks in the subsequent target chromatogram and the reference chromatogram (step S22). The index for estimating the degree of matching of the peaks of the two chromatograms uses the sum of the distances (times) between the peaks in the target chromatogram located at the nearest positions temporally to each peak appearing in the reference chromatogram and having intensities such that the ratios of the intensities of the peaks fall within a certain range as an evaluation function. An evaluation of peak conformity is executed using the same evaluation function for all combinations of candidates (step S3), and a combination of candidates at the front and the tail end for which the evaluation function is smallest is selected (step S24). In actuality, in order to simplify the calculations, an evaluation function determined by adding the evaluation function of the degree of conformity described above and an evaluation function indicating the degree to which candidates are at the front or the tail end should be used.

The start point and the end point of the section where the peaks are present in the reference chromatogram and the target chromatogram are established by the processing described above, so the parameters for linear correction (specifically, the expansion/contraction rate p and the amount of shift q) are thereby calculated (step S25), and the position of each peak in the target chromatogram is corrected in accordance with the parameters (step S26). As a result, the linear component of time deviations contained in the target chromatogram is almost completely eliminated.

[Step S3] Search by Coarse Stage DP

Figure 6:
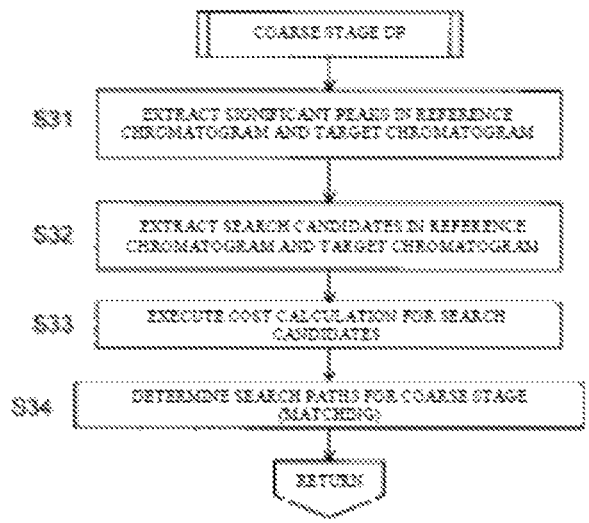
FIG. 6 is a flowchart of the coarse stage DP of FIG. 2.
Figure 8:
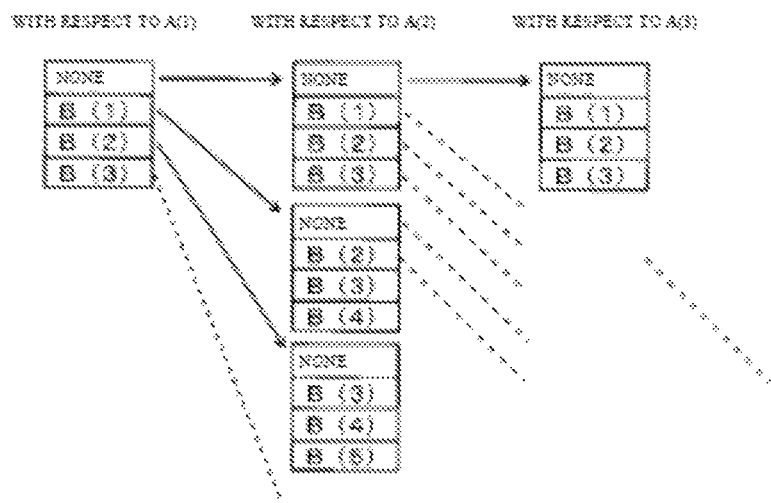
FIG. 8 is an explanatory diagram of typical DP.

FIG. 6 is a flowchart showing the processing procedure for coarse stage DP. In coarse stage DP, in order to reduce the amount of data to be processed, the data is first simply thinned out at a constant ratio in order to peak intensity, and processing is performed whereby peaks with an intensity equal to or less than a certain relative intensity are considered highly likely to be noise and are removed. As a result, peaks which can be presumed to be significant to correction are selected, and the number of peaks is limited to a prescribed number (step S31). Matching based on a DP algorithm is then executed using the times of the peaks of the reference chromatogram and the target chromatogram as input data. That is, the peak correspondence candidates extracted in the target chromatogram are given in order from the earliest peaks for peaks extracted in the reference chromatogram, and when a plurality of candidates are given, the search is repeated so that the next peak correspondence candidate is given for each candidate. Accordingly, as shown in FIG. 8, the candidates expand in a tree shape (step S32).

At this time, by restricting the expansion of candidates to a time range taking into consideration the maximum assumed value of nonlinear time deviations, the number of candidates given at each peak point is restricted. As described above, since the linear time deviations are eliminated in advance, it is possible to avoid situations in which legitimate candidates are eliminated even if this restriction is made strict (even if the beam width is narrowed).

Next, the cost is calculated for each of the retrieved candidates for a correspondence relationship (step S33).

The cost function in coarse stage DP is as follows.

(1) A value determined by multiplying the logarithm of the intensity ratio of corresponding peaks by a certain constant. However, if there is no corresponding peak, this is a value determined by adding a certain constant to the peak intensity for every skipped peak.

(2) Amount of time fluctuation: Absolute value of the time difference between a peak in the reference chromatogram and a peak in the target chromatogram (3) Difference in the amount of time fluctuation: Since most time fluctuations occur gradually, the difference in the amount of time fluctuation should assume a value close to zero. Therefore, as a value corresponding to the mean amount of time fluctuation, the absolute value of the difference between a value determined by applying a low-pass filter to the amount of time fluctuation and the present time fluctuation at the corresponding peak is used.

(4) Intensity ratio difference: There is a very strong correlation between the intensities of each of the peaks in the reference chromatogram and the target chromatogram after matching, and the intensity ratio is ideally constant. Therefore, as a value corresponding to the mean of the logarithm of the intensity ratio, the absolute value of the difference between a value determined by applying a low pass filter to the logarithm of the intensity ratio and the logarithm of the intensity ratio at the present corresponding peak is used.

In actuality, a cost function is obtained by multiplying with a constant after performing a predetermined gamma correction on (1) to (4) above.

If the cost calculation is complete for all of the candidates for a correspondence relationship between the reference chromatogram and the target chromatogram, the candidate with the lowest cost is selected, and this is determined as the optimal match of coarse stage DP (step S34).

[Step S4] Filtering Processing

Figure 7:
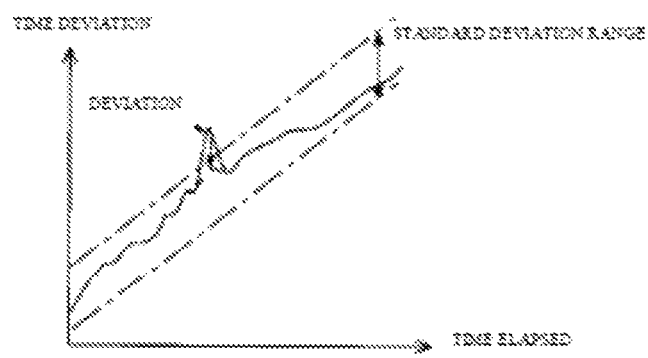
FIG. 7 is an explanatory diagram of the concept of mistaken candidate filtering processing in FIG. 2.

Although DP is excellent for local matching, there are cases in which matching is performed so as to deviate from the validity of correction as indicated by the overall trend of the chromatogram. Therefore, as shown in FIG. 7, the standard deviation of the time deviation at each peak point is calculated for the correspondence relationship determined as an optimal match, and if there is any deviation from the standard deviation, the matching of the peak in question is eliminated.

[Step S5] Search by Fine Stage DP

Next, after the search space is narrowed down using the matching results obtained by coarse stage DP, matching is executed using a DP algorithm including peaks which were excluded at the time of coarse stage DP. At this time, the time fluctuation in fine stage DP assumes a value close to the time fluctuation found in coarse stage DP, so the gamma correction and constant applied to the cost function of the results of coarse stage DP are changed, and the cost of the degree of divergence from the matching results of coarse stage DP is further added as follows.

(1) For a peak in the reference chromatogram with a match in coarse stage DP, the cost is considered to be infinite if the matching does not conform in fine stage DP, and this candidate is discarded.

(2) For a peak in the reference chromatogram with no match in coarse stage DP, the absolute value of the time deviation from the time determined by the linear interpolation of the result of matching in coarse stage DP (temporally close peak) is used as the cost of the degree of divergence.

Accordingly, the correspondence of a matching peak in coarse stage DP is considered accurate, and an appropriate correspondence is determined for peaks not used in coarse stage DP. As a result, it is possible to determine an optimal correspondence relationship between the final chromatogram and the target chromatogram.

Figure 9:
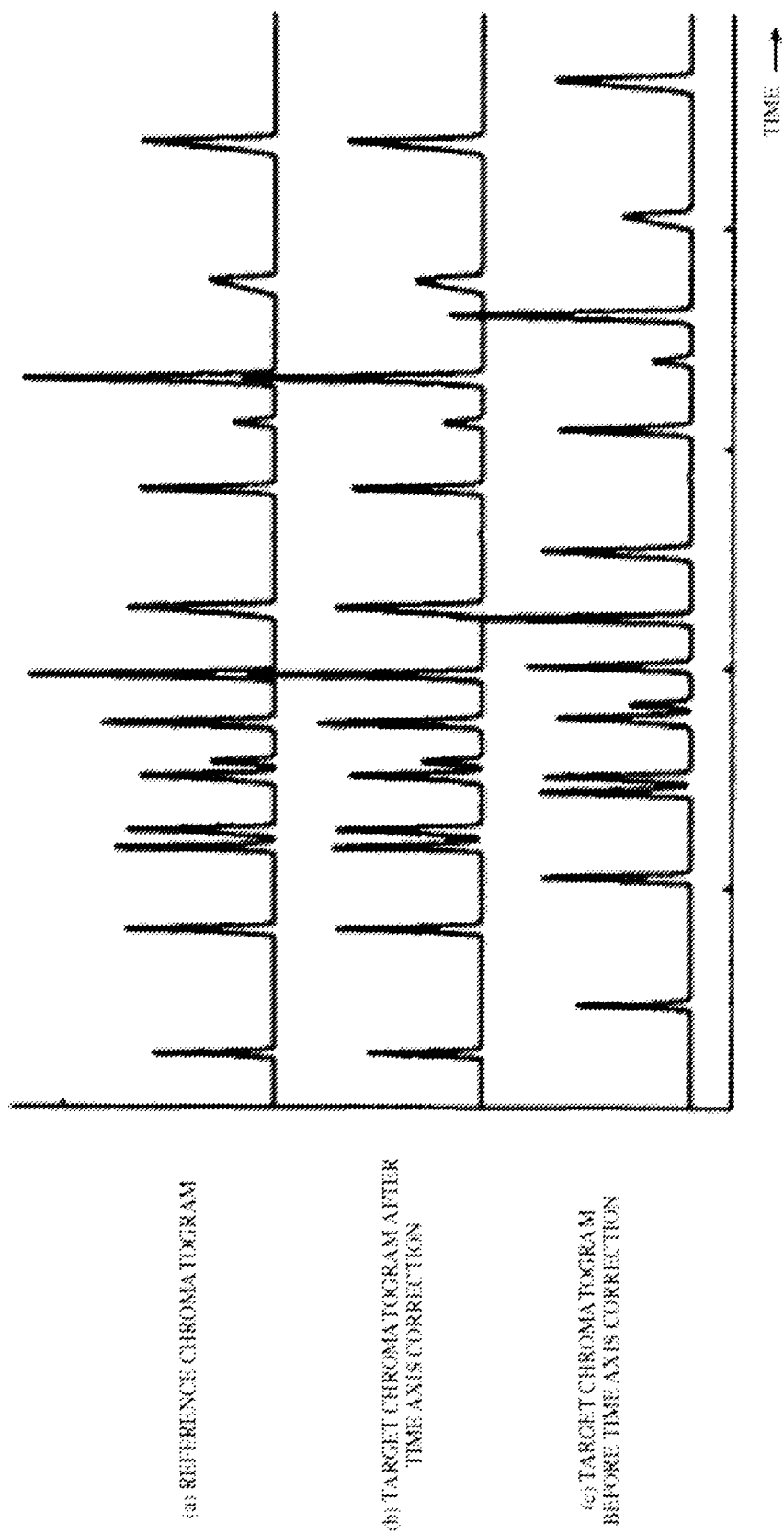
FIG. 9 is a drawing showing the results of a simulation for verifying the effects of the time axis correction method characteristic to the present invention.

FIG. 9 is a drawing showing the processing results when time axis correction is executed using the chromatogram data processing method of the present invention. As shown in this figure, it can be seen that the corrected target chromatogram closely matches the reference chromatogram.

All of the embodiments described above are merely examples of the present invention, and it goes without saying that appropriate modifications, amendments, and additions within the scope of the gist of the present invention are also included in the scope of the patent claims of this application.

EXPLANATION OF SYMBOLS

1 . . . sample introducing part
2 . . . column
3 . . . detector
4 . . . A/D converter
5 . . . data processing part
51 . . . chromatogram data storage part
52 . . . time axis correction operation processing part
53 . . . chromatogram creation/drawing part
6 . . . display part

What is claimed is:

1. A chromatogram data processing method for coordinating a time axis of a reference chromatogram serving as a standard so that a time axis of a target chromatogram is aligned with the time axis of the reference chromatogram, comprising:

a data receiving step for receiving target chromatogram data from a chromatograph device including a separation part for separating various components contained in a sample in the time direction and a detector for detecting a sample with separated components, a linear correction step for eliminating linear time variation from the target chromatogram using peaks detected in the reference chromatogram and the target chromatogram;

a coarse searching step for searching for candidates for a correspondence relationship between the reference chromatogram and the target chromatogram in a coarse stage by selecting peaks for the respective reference chromatogram and target chromatogram, the selected peaks being selected based on intensity information for each of the respectively detected peaks in the target chromatogram and the reference chromatogram after linear correction by said linear correction step, and determining the candidates in the coarse stage by executing matching by a dynamic programming algorithm focusing on the retention times of the selected peaks, wherein peaks not selected by said selecting are eliminated from consideration during said matching;

a fine searching step for searching for a correspondence relationship between the reference chromatogram and the target chromatogram in a fine stage by adding the peaks that were eliminated from consideration in said coarse searching step and then executing matching by a dynamic programming algorithm focusing on the retention times of peaks corresponding to the candidates determined in said coarse searching step and the peaks that were eliminated from consideration in said coarse searching step, to determine the correspondence relationship by verifying accuracy of the candidates determined in said coarse searching step and determining an appropriate correspondence for the peaks that were eliminated from consideration in said coarse searching step; and a correction processing step for correcting the time axis of the target chromatogram so as to align the time axis of the target chromatogram with the time axis of the reference chromatogram based on the correspondence relationship between the reference chromatogram and the target chromatogram determined in said fine searching step.

2. The chromatogram data processing method according to claim 1 having:

a filtering step which, after the execution of said coarse searching step and before the execution of said fine searching step, uses the overall trend of matching as an evaluation criterion and removes matching results which do not conform to the evaluation criterion.

3. The chromatogram data processing method according to claim 1, wherein:

said linear correction step finds a coefficient for linear correction by extracting a corresponding time range between the reference chromatogram and the target chromatogram using the intensity correlations and time relationships of a plurality of peaks close to one another in the time direction, investigating the degree of matching of peaks when performing linear correction while assuming combinations of the time ranges, and selecting the combination of time ranges which demonstrates a closest match in the intensity correlations and time relationships of the plurality of peaks close to one another.

4. The chromatogram data processing method according to claim 2, wherein:

said linear correction step finds a coefficient for linear correction by extracting a corresponding time range between the reference chromatogram and the target chromatogram using the intensity correlations and time relationships of a plurality of peaks close to one another in the time direction, investigating a degree of matching of peaks when performing linear correction while assuming combinations of the time ranges, and selecting as the target chromatogram and the reference chromatogram after linear correction the coefficient for linear correction that provides a closest match in the intensity correlations and time relationships of the plurality of peaks close to one another.

5. The chromatogram data processing method according to claim 3, wherein:

as a measure indicating the degree of matching of peaks in said linear correction step, for each peak in the reference chromatogram, the sum of the absolute values of time differences of a single peak in said reference chromatogram and a peak positioned closest to the aforementioned peak and falling within a certain intensity ratio range with respect to the intensity of the peak in said reference chromatogram in the target chromatogram after linear correction is performed under the assumptions described above is used.

6. The chromatogram data processing method according to claim 4, wherein:

as a measure indicating the degree of matching of peaks in said linear correction step, for each peak in the reference chromatogram, the sum of the absolute values of time differences of a single peak in said reference chromatogram and a peak positioned closest to the aforementioned peak and falling within a certain intensity ratio range with respect to the intensity of the peak in said reference chromatogram in the target chromatogram after linear correction is performed under the assumptions described above is used.

7. A chromatogram data processing device for coordinating a time axis of a reference chromatogram serving as a standard so that a time axis of the target chromatogram is aligned with the time axis of the reference chromatogram, comprising:

a chromatograph device comprising a separation part for separating various components contained in a sample in the time direction and a detector for detecting a sample with separated components, the chromatograph device providing target chromatogram data;

a linear correction means for eliminating linear time variations from the target chromatogram using peaks detected in the reference chromatogram and the target chromatogram;

a coarse searching means for searching for candidates for a correspondence relationship between the reference chromatogram and the target chromatogram in a coarse stage by selecting peaks for the respective reference chromatogram and target chromatogram, the selected peaks being selected based on intensity information for each of the respectively detected peaks in the target chromatogram and the reference chromatogram after linear correction by said linear correction means, and determining the candidates in the coarse stage by executing matching by a dynamic programming algorithm focusing on the retention times of the selected peaks, wherein peaks not selected by said selecting are eliminated from consideration by said coarse searching means;

a fine searching means for searching for a correspondence relationship between the reference chromatogram and the target chromatogram in a fine stage by adding peaks that were eliminated from consideration by said coarse searching means and then executing matching by a dynamic programming algorithm focusing on the retention times of peaks corresponding to the candidates determined by said coarse searching means and the peaks that were eliminated from consideration by said coarse searching means, to determine the correspondence relationship by verifying accuracy of the candidates determined by said coarse searching means and determining an appropriate correspondence for the peaks that were eliminated by said coarse searching means; and a correction processing means for correcting the time axis of the target chromatogram so as to align the time axis of the target chromatogram with the time axis of the reference chromatogram based on the correspondence relationship between the reference chromatogram and the target chromatogram determined by said fine searching means.

* * * * *